(12) United States Patent
Das et al.

(10) Patent No.: US 8,916,154 B2
(45) Date of Patent: Dec. 23, 2014

(54) ANTIBODIES AGAINST DELTA-5 DESATURASE AND USES THEREOF

(75) Inventors: Tapas Das, Harbourfront (SG); Suzette L. Pereira, Westerville, OH (US); Pradip Mukerji, Columbus, OH (US); Padmavathy Krishnan, Hilliard, OH (US)

(73) Assignee: Abbott Laboratories, Abbott Park, IL (US)

( * ) Notice: Subject to any disclaimer, the term of this patent is extended or adjusted under 35 U.S.C. 154(b) by 109 days.

(21) Appl. No.: 12/686,781

(22) Filed: Jan. 13, 2010

(65) Prior Publication Data

US 2010/0273187 A1    Oct. 28, 2010

Related U.S. Application Data

(60) Provisional application No. 61/173,038, filed on Apr. 27, 2009.

(51) Int. Cl.
*A61K 39/395* (2006.01)
*C07K 16/40* (2006.01)
*C07K 16/14* (2006.01)

(52) U.S. Cl.
CPC .............. *C07K 16/14* (2013.01); *C07K 16/40* (2013.01); *C07K 2319/23* (2013.01)
USPC ................ 424/146.1; 424/130.1; 424/141.1; 424/152.1; 530/387.1; 530/388.1; 530/388.26; 530/388.5

(58) Field of Classification Search
USPC ................ 530/387.1, 388.1, 388.26, 388.5; 424/130.1, 141.1, 146.1, 152.1
See application file for complete search history.

(56) References Cited

U.S. PATENT DOCUMENTS

| | | | |
|---|---|---|---|
| 5,256,561 | A | 10/1993 | Chin |
| 6,015,662 | A | 1/2000 | Hackett, Jr. et al. |
| 6,635,451 | B2 | 10/2003 | Mukerji et al. |
| 6,818,392 | B2 | 11/2004 | Lou et al. |
| 7,067,285 | B2 | 6/2006 | Mukerji et al. |
| 7,241,619 | B2 | 7/2007 | Mukerji et al. |

FOREIGN PATENT DOCUMENTS

| | | |
|---|---|---|
| WO | 0020603 A1 | 4/2000 |
| WO | WO0020603 A1 | 4/2000 |
| WO | 02081668 A2 | 10/2002 |
| WO | WO02081668 A2 | 10/2002 |
| WO | 2004071467 A2 * | 8/2004 |
| WO | 2004101757 A2 * | 11/2004 |

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Pereira SL, Leonard AE, Mukerji P. (2003) Recent advances in the study of fatty acid desaturases from animals and lower eukaryotes. Prostaglandins Leukot Essent Fatty Acids. 68 (2):97-106.
International Search Report and Written Opinion for PCT/US2010/027085 dated May 20, 2010.

* cited by examiner

*Primary Examiner* — Jennifer Graser
(74) *Attorney, Agent, or Firm* — Calfee, Halter & Griswold LLP

(57) ABSTRACT

Disclosed are antibodies that specifically recognize Δ5-desaturase, methods of producing the antibodies, nucleotides and polypeptides for producing the antibodies, and methods of using the antibodies. The Δ5-desaturase-specific antibodies provide improved methods of detecting Δ5-desaturase in a sample.

19 Claims, 6 Drawing Sheets

Lanes 1-6: GST-His-SDD5-C1
   Lane 1: Insoluble
   Lane 2: Denatured
   Lane 3: Flow through
   Lane 4: Wash1
   Lane 5: Elution 1
   Lane 6: Elution 2

M: Marker [MW(KDa)116, 66.2, 45, 35, 25, 18.4, 14.4]

Lanes 7-12: GST-His-SDD5-C2
   Lane 7: Insoluble
   Lane 8: Denatured
   Lane 9: Flow through
   Lane 10: Wash1
   Lane 11: Elution 1
   Lane 12: C2- Elution 2

C1: GST-His-SDD5-C1 (47.2 KDa)
C2: GST-His-SDD5-C2 (41.1 KDa)
M: Marker (MW (kDa) 14.4, 18.4, 25, 35, 45, 66.2, 116)

Lane 1:   Yeast microsome, vector (pYX242), 100 μg
Lane 2:   Yeast microsome, pRSP3 (pYX242 + sdd5), 100 μg
Lane 3:   Yeast microsome, vector, 20 μg
Lane 4:   Yeast microsome, pRSP3, 20 μg
Lane 5:   Vector supernate of 10,000x g spin, 30 μg
Lane 6:   pRSP3 supernate of 10,000x g spin, 30 μg
Lane 7:   GST-His-SDD5-C1 peptide, 40 ng Lane 1:   Yeast microsome, vector (pYX242), 100 µg
Lane 2:   Yeast microsome, pRSP3 (pYX242 + *sdd5*), 100 µg
Lane 3:   Yeast microsome, vector, 20 µg
Lane 4:   Yeast microsome, pRSP3, 20 µg
Lane 5:   Vector supernate of 10,000x g spin, 30 µg
Lane 6:   pRSP3 supernate of 10,000x g spin, 30 µg
Lane 7:   GST-His-SDD5-C1 peptide, 40 ng Lane 1: Yeast microsome, vector (pYX242) only, 20 μg
Lane 2: Yeast microsome, vector only, 100 μg
Lane 3: Yeast microsome, pRSP3 (pYX242 + sdd5), 20 μg
Lane 4: Yeast microsome, pRSP3, 100 μg
Lane 5: GST-His-SDD5-C1 peptide, 20 ng
Lane 6: GST control (~64 kDa)
Lane 7: Yeast microsome, pRSP1 (pYX242 + sdd6), 100 μg

FIG. 6

```
               1                                                  50
SDD5-C1   (1)  MAPQTELRQRHAAVAETPVAGKKAFTWQEVAQHNTAASAWIIIRGKVYDV
MA-D5     (1)  ------------------MGTDQGKTFTWEELAAHNTKGDLFLAIRGRVYDV 51                                                100
SDD5-C1  (51)  TEWANKHPGGREMVLLHAGREATDTFDSYHPFSDKAESILNKYEIGTFTG
MA-D5    (35)  TKFLSRHPGGVDTLLLGAGRDVIPVFEMYHAFG-ADAIMKKYYVGTLVS 101                                136
SDD5-C1 (101)  PSEFPTFKPDTGFYKECRKRVGEYFKKNNLHPQDGF
MA-D5    (84)  N-ELPVFPEPTVFHKTIKTRVEGYFTDRDIDPKNRP
```

SDD5-C1: Residues 1-136 of *Saprolegnia diclina* Δ5-desaturase (SEQ. ID. NO: 2)
MA-D5: Resisues 1-118 of *Mortierella alpina* Δ5-desaturase (SEQ. ID. NO: 16)

Percent sequence identity: 35.3%

SEQUENCE LISTING

<160> NUMBER OF SEQ ID NOS: 18

<210> SEQ ID NO 1
<211> LENGTH: 470
<212> TYPE: PRT
<213> ORGANISM: Saprolegnia diclina

<400> SEQUENCE: 1

```
Met Ala Pro Gln Thr Glu Leu Arg Gln Arg His Ala Ala Val Ala Glu
1               5                   10                  15

Thr Pro Val Ala Gly Lys Lys Ala Phe Thr Trp Gln Glu Val Ala Gln
            20                  25                  30

His Asn Thr Ala Ala Ser Ala Trp Ile Ile Ile Arg Gly Lys Val Tyr
        35                  40                  45

Asp Val Thr Glu Trp Ala Asn Lys His Pro Gly Gly Arg Glu Met Val
    50                  55                  60

Leu Leu His Ala Gly Arg Glu Ala Thr Asp Thr Phe Asp Ser Tyr His
65                  70                  75                  80

Pro Phe Ser Asp Lys Ala Glu Ser Ile Leu Asn Lys Tyr Glu Ile Gly
                85                  90                  95

Thr Phe Thr Gly Pro Ser Glu Phe Pro Thr Phe Lys Pro Asp Thr Gly
            100                 105                 110

Phe Tyr Lys Glu Cys Arg Lys Arg Val Gly Glu Tyr Phe Lys Lys Asn
        115                 120                 125

Asn Leu His Pro Gln Asp Gly Phe Pro Gly Leu Trp Arg Met Met Val
    130                 135                 140

Val Phe Ala Val Ala Gly Leu Ala Leu Tyr Gly Met His Phe Ser Thr
145                 150                 155                 160

Ile Phe Ala Leu Gln Leu Ala Ala Ala Leu Phe Gly Val Cys Gln
                165                 170                 175

Ala Leu Pro Leu Leu His Val Met His Asp Ser Ser His Ala Ser Tyr
                180                 185                 190

Thr Asn Met Pro Phe Phe His Tyr Val Val Gly Arg Phe Ala Met Asp
            195                 200                 205

Trp Phe Ala Gly Gly Ser Met Val Ser Trp Leu Asn Gln His Val Val
        210                 215                 220
```

Gly His His Ile Tyr Thr Asn Val Ala Gly Ser Asp Pro Asp Leu Pro
225                 230                 235                 240

Val Asn Met Asp Gly Asp Ile Arg Arg Ile Val Asn Arg Gln Val Phe
            245                 250                 255

Gln Pro Met Tyr Ala Phe Gln His Ile Tyr Leu Pro Pro Leu Tyr Gly
            260                 265                 270

Val Leu Gly Leu Lys Phe Arg Ile Gln Asp Phe Thr Asp Thr Phe Gly
        275                 280                 285

Ser His Thr Asn Gly Pro Ile Arg Val Asn Pro His Ala Leu Ser Thr
        290                 295                 300

Trp Met Ala Met Ile Ser Ser Lys Ser Phe Trp Ala Phe Tyr Arg Val
305                 310                 315                 320

Tyr Leu Pro Leu Ala Val Leu Gln Met Pro Ile Lys Thr Tyr Leu Ala
                325                 330                 335

Ile Phe Phe Leu Ala Glu Phe Val Thr Gly Trp Tyr Leu Ala Phe Asn
                340                 345                 350

Phe Gln Val Ser His Val Ser Thr Glu Cys Gly Tyr Pro Cys Gly Asp
            355                 360                 365

Glu Ala Lys Met Ala Leu Gln Asp Glu Trp Ala Val Ser Gln Val Lys
        370                 375                 380

Thr Ser Val Asp Tyr Ala His Gly Ser Trp Met Thr Thr Phe Leu Ala
385                 390                 395                 400

Gly Ala Leu Asn Tyr Gln Val Val His His Leu Phe Pro Ser Val Ser
                405                 410                 415

Gln Tyr His Tyr Pro Ala Ile Ala Pro Ile Ile Val Asp Val Cys Lys
            420                 425                 430

Glu Tyr Asn Ile Lys Tyr Ala Ile Leu Pro Asp Phe Thr Ala Ala Phe
        435                 440                 445

Val Ala His Leu Lys His Leu Arg Asn Met Gly Gln Gln Gly Ile Ala
        450                 455                 460

Ala Thr Ile His Met Gly
465                 470

<210> SEQ ID NO 2
<211> LENGTH: 136
<212> TYPE: PRT
<213> ORGANISM: Artificial Sequence
<220> FEATURE:
<223> OTHER INFORMATION: Synthetic

<400> SEQUENCE: 2

Met Ala Pro Gln Thr Glu Leu Arg Gln Arg His Ala Ala Val Ala Glu
1               5                   10                  15

Thr Pro Val Ala Gly Lys Lys Ala Phe Thr Trp Gln Glu Val Ala Gln
            20                  25                  30

His Asn Thr Ala Ala Ser Ala Trp Ile Ile Arg Gly Lys Val Tyr
            35                  40                  45

Asp Val Thr Glu Trp Ala Asn Lys His Pro Gly Gly Arg Glu Met Val
        50                  55                  60

Leu Leu His Ala Gly Arg Glu Ala Thr Asp Thr Phe Asp Ser Tyr His
65                  70                  75                  80

Pro Phe Ser Asp Lys Ala Glu Ser Ile Leu Asn Lys Tyr Glu Ile Gly
                85                  90                  95

Thr Phe Thr Gly Pro Ser Glu Phe Pro Thr Phe Lys Pro Asp Thr Gly
                100                 105                 110

```
Phe Tyr Lys Glu Cys Arg Lys Arg Val Gly Glu Tyr Phe Lys Lys Asn
            115                 120                 125

Asn Leu His Pro Gln Asp Gly Phe
    130                 135

<210> SEQ ID NO 3
<211> LENGTH: 408
<212> TYPE: DNA
<213> ORGANISM: Artificial
<220> FEATURE:
<223> OTHER INFORMATION: Synthetic

<400> SEQUENCE: 3
atggccccgc agacggagct ccgccagcgc cacgccgccg tcgccgagac gccggtggcc        60
ggcaagaagg cctttacatg gcaggaggtc gcgcagcaca cacggcggc ctcggcctgg       120 atcattatcc gcggcaaggt ctacgacgtg accgagtggg ccaacaagca ccccggcggc       180
cgcgagatgg tgctgctgca cgccggtcgc gaggccaccg acacgttcga ctcgtaccac       240
ccgttcagcg acaaggccga gtcgatcttg aacaagtatg agattggcac gttcacgggc       300
ccgtccgagt ttccgacctt caagccggac acgggcttct acaaggagtg ccgcaagcgc       360
gttggcgagt acttcaagaa gaacaacctc catccgcagg acggcttc                   408

<210> SEQ ID NO 4
<211> LENGTH: 81
<212> TYPE: PRT
<213> ORGANISM: Artificial Sequence
<220> FEATURE:
<223> OTHER INFORMATION: Synthetic

<400> SEQUENCE: 4

Asn Gln His Val Val Gly His His Ile Tyr Thr Asn Val Ala Gly Ser
1               5                   10                  15

Asp Pro Asp Leu Pro Val Asn Met Asp Gly Asp Ile Arg Arg Ile Val
            20                  25                  30

Asn Arg Gln Val Phe Gln Pro Met Tyr Ala Phe Gln His Ile Tyr Leu
        35                  40                  45

Pro Pro Leu Tyr Gly Val Leu Gly Leu Lys Phe Arg Ile Gln Asp Phe
    50                  55                  60

Thr Asp Thr Phe Gly Ser His Thr Asn Gly Pro Ile Arg Val Asn Pro
65                  70                  75                  80

His

<210> SEQ ID NO 5
<211> LENGTH: 243
<212> TYPE: DNA
<213> ORGANISM: Artificial Sequence
<220> FEATURE:
<223> OTHER INFORMATION: Synthetic

<400> SEQUENCE: 5
aaccagcacg tcgtgggcca ccacatctac acgaacgtcg cgggctcgga cccggatctt        60
ccggtcaaca tggacggcga catccgccgc atcgtgaacc gccaggtgtt ccagcccatg       120
tacgcattcc agcacatcta ccttccgccg ctctatggcg tgcttggcct caagttccgc       180
atccaggact tcaccgacac gttcggctcg cacacgaacg gcccgatccg cgtcaacccg       240
cac                                                                     243

<210> SEQ ID NO 6
```

```
<211> LENGTH: 22
<212> TYPE: DNA
<213> ORGANISM: Artificial Sequence
<220> FEATURE:
<223> OTHER INFORMATION: Synthetic

<400> SEQUENCE: 6
agagtcccat ggccccgcag ac                                              22

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
tgtacagaat tcttagaagc cgtcc                                           25

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
agagtcccat ggggaaccag cacg                                            24

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9
tgtacagaat tcttagtgcg ggttgac                                         27

<210> SEQ ID NO 10
<211> LENGTH: 27
<212> TYPE: DNA
<213> ORGANISM: Artificial Sequence
<220> FEATURE:
<223> OTHER INFORMATION: Synthetic

<400> SEQUENCE: 10
agcgcgcgga attcatgtcc cctatac                                         27

<210> SEQ ID NO 11
<211> LENGTH: 38
<212> TYPE: DNA
<213> ORGANISM: Artificial Sequence
<220> FEATURE:
<223> OTHER INFORMATION: Synthetic

<400> SEQUENCE: 11
ggatccacgc ggaaccagat ccgatttttgg aggatggt                            38

<210> SEQ ID NO 12
<211> LENGTH: 37
<212> TYPE: DNA
<213> ORGANISM: Artificial Sequence
<220> FEATURE:
<223> OTHER INFORMATION: Synthetic

<400> SEQUENCE: 12
```

```
aaatcggatc tggttccgcg tggatccatg gccccgc                                37
```

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13

```
atagtaaagc tttcagaagc cgtcctgcgg at                                     32
```

<210> SEQ ID NO 14
<211> LENGTH: 37
<212> TYPE: DNA
<213> ORGANISM: Artificial Sequence
<220> FEATURE:
<223> OTHER INFORMATION: Synthetic

<400> SEQUENCE: 14

```
aaatcggatc tggttccgcg tggatccaac cagcacg                                37
```

<210> SEQ ID NO 15
<211> LENGTH: 28
<212> TYPE: DNA
<213> ORGANISM: Artificial Sequence
<220> FEATURE:
<223> OTHER INFORMATION: Synthetic

<400> SEQUENCE: 15

```
tgtatcaagc tttcagtgcg ggttgacg                                          28
```

<210> SEQ ID NO 16
<211> LENGTH: 118
<212> TYPE: PRT
<213> ORGANISM: Mortierella alpina

<400> SEQUENCE: 16

Met Gly Thr Asp Gln Gly Lys Thr Phe Thr Trp Glu Glu Leu Ala Ala
1               5                   10                  15

His Asn Thr Lys Gly Asp Leu Phe Leu Ala Ile Arg Gly Arg Val Tyr
            20                  25                  30

Asn Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Val Phe Pro Glu Pro Thr Val Phe His
                85                  90                  95

Lys Thr Ile Lys Thr Arg Val Glu Gly Tyr Phe Thr Asp Arg Asn Ile
            100                 105                 110

Asp Pro Lys Asn Arg Pro
        115

<210> SEQ ID NO 17
<211> LENGTH: 6
<212> TYPE: PRT
<213> ORGANISM: Artificial Sequence
<220> FEATURE:
<223> OTHER INFORMATION: Synthetic

```
<400> SEQUENCE: 17

His His His His His His
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic

<400> SEQUENCE: 18

Leu Val Pro Arg Gly Ser
1               5
```

US 8,916,154 B2

ANTIBODIES AGAINST DELTA-5 DESATURASE AND USES THEREOF

CROSS-REFERENCE TO RELATED APPLICATIONS

The present application claims priority to U.S. Provisional Application No. 61/173,038, filed Apr. 27, 2009, which is incorporated by reference in its entirety.

INCORPORATION OF SEQUENCE LISTING

A paper copy of the Sequence Listing and a computer readable form of the sequence listing containing the file named "9881USL1_ST25.txt" which is 11,264 bytes in size (measured in MS-DOS) are provided herein and are herein incorporated by reference. This Sequence Listing consists of SEQ ID NOs: 1-18.

TECHNICAL FIELD

The present invention is directed to antibodies that specifically recognize Δ5-desaturase enzymes, methods for producing such antibodies, and polypeptides and nucleotides used in the production of such antibodies.

BACKGROUND OF THE INVENTION

Δ5-desaturase belongs to the family of "front-end" desaturases. In addition to Δ5-desaturase, the family also includes Δ4-, Δ6-, and Δ8-desaturases. These desaturases introduce double-bonds between the carboxyl end (i.e., the "front end") and a pre-existing double bond in fatty acids. This is a required step in the biosynthesis of polyunsaturated fatty acids (PUFAs) such as arachidonic acid (ARA), eicosapentaenoic acid (EPA), and docosahexaenoic acid (DHA).

ARA, EPA, and DHA are oils widely used in nutritional products. The current sources of these oils are very expensive and non-renewable. The production of oils enriched in ARA, EPA, and DHA from transgenic plants or oleaginous microorganisms expressing heterologous front-end desaturases offers a low-cost, renewable alternative to purifying the oils from natural sources. Transgenic organisms producing these oils are currently in development. See U.S. Pat. Nos. 6,635,451; 7,067,285; and 7,241,619.

Before commercialization of ARA-, EPA-, or DHA-enriched oils derived from transgenic organisms can begin, approval is needed from such regulatory agencies as the United States Food and Drug Administration (FDA) and the United States Department of Agriculture (USDA).

One regulatory requirement for transgenic plants is to detect and quantitate the specific transgenic proteins present in the organism, including the oil-rich seeds.

However, quantitation of the front-end desaturases is a problem because specific antibodies to the desaturases do not exist. The most straightforward way to produce an antibody against a protein is to use the protein itself as an immunogen. This is not possible with the front-end desaturases. All the front-end desaturases are highly hydrophobic; they contain several transmembrane domains and reside in the microsomal membranes of cells (Pereira S L, Leonard A E, Mukerji P. (2003) Recent advances in the study of fatty acid desaturases from animals and lower eukaryotes. *Prostaglandins Leukot Essent Fatty Acids.* 68 (2):97-106). The hydrophobic nature of the front-end desaturases makes large-scale purification of them a challenge. As a result, the full-length proteins cannot be used as immunogens in antibody production.

The production of antibodies that specifically recognize a front-end desaturase, such as Δ5-desaturase, would enable one to identify and quantitate the enzyme in various systems. This would be especially useful when a Δ5-desaturase gene is expressed in a transgenic host (such as a plant, yeast, or mammalian cell) during production of PUFA-enriched oils. A need therefore exists for antibodies that specifically recognize Δ5-desaturase.

SUMMARY OF THE INVENTION

One embodiment of the invention is directed to an antibody that specifically binds Δ5-desaturase derived from fungus or algae.

It has been found, surprisingly, that an antibody generated against a polypeptide fragment comprising SEQ ID NO: 2 specifically binds the full-length Δ5-desaturase derived from fungus and does not bind the full-length Δ6-desaturase derived from the same source.

The Δ5-desaturase-specific antibodies described herein are especially useful in detecting and quantitating the presence of Δ5-desaturase expressed in transgenic organisms (e.g., plants or yeast, etc.) that produce oils enriched in ARA, EPA, or DHA.

BRIEF DESCRIPTION OF THE DRAWINGS

FIG. 6 shows an alignment of the SDD5-C1 polypeptide (amino acid residues 1-136 of *Saprolegnia diclina* Δ5-desaturase) with the corresponding N-terminal region (amino acid residues 1-118) of *Mortierella alpina* Δ5-desaturase.

DETAILED DESCRIPTION OF THE INVENTION

Figure 1:
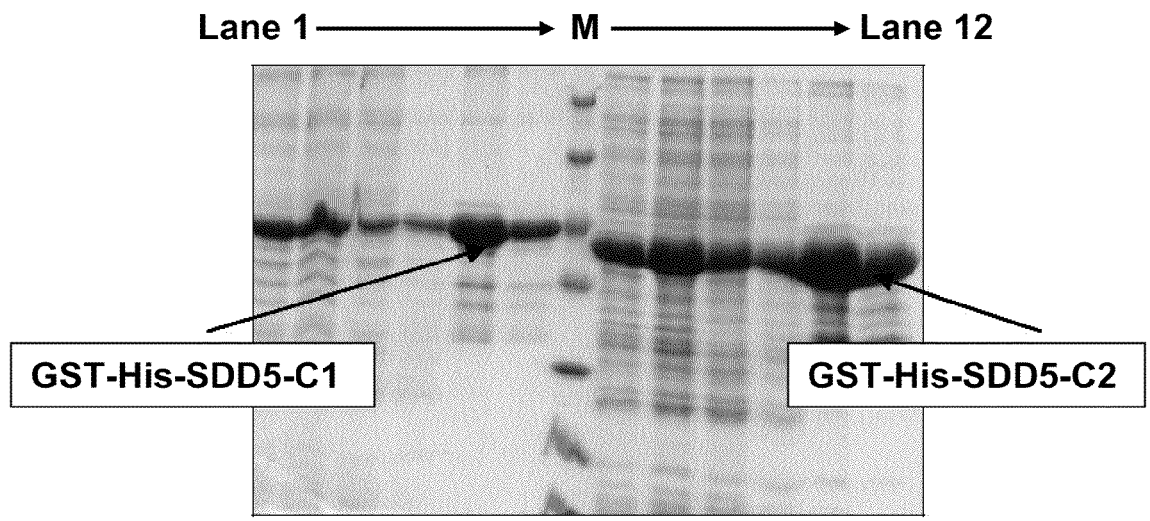
FIG. 1 shows an SDS-PAGE gel of *E. coli*-expressed, recombinant polypeptide fragments of *Saprolegnia diclina* Δ5-desaturase (GST-His-SDD5-C1 and GST-His-SDD5-C2) stained with Coomassie blue after small-scale purification.

The various embodiments described herein comprise antibodies that specifically bind Δ5-desaturase. These and other essential or optional elements or limitations of the antibodies are described in detail hereinafter.

The term "identity," used in reference to amino acid sequences, refers to the presence of a series of exactly alike or invariant amino acid residues.

The term "conservative amino acid substitution" refers to the replacement of an amino acid residue with an amino acid residue having a similar side chain. Polypeptides including one or more such conservative substitutions are termed "conservative variations" or "conservative variants" of a respective parent polypeptide. Families of amino acid residues having similar side chains include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "homologous," "substantially similar," and "corresponding substantially" are used interchangeably. They refer to a polypeptide fragment wherein a change in one or more amino acid does not affect the ability of the polypeptide to produce a certain effect. These terms also refer to modifications of the polypeptides described herein such as deletion or insertion of one or more amino acids that do not substantially alter the functional properties of the resulting polypeptide fragment relative to the initial, unmodified fragment. It is therefore understood that embodiments described herein encompass more than the specific exemplary sequences.

The term "gene" refers to a nucleic acid fragment that expresses a specific protein or polypeptide.

The term "native," used in reference to a gene or protein, refers to a gene or protein as found in nature.

The term "natively expresses" refers to expression of a native gene or native protein that is not foreign.

The terms "foreign" and "heterologous," used in reference to any gene or its product, refer to genes and their products that are not normally found in a host organism but that are introduced into the host organism by gene transfer. Foreign genes and proteins can comprise native genes and proteins inserted into a non-native organism.

The term "transgene" refers to a gene that has been introduced into the genome by a transformation procedure.

The term "isolated," used in reference to a nucleotide, gene, polypeptide, or protein, refers to its removal from its natural environment.

The term "expression" or "expresses" refers to the production of a functional end-product. Expression of a gene involves transcription of the gene and translation of the mRNA into a precursor or mature protein.

The term "host" refers to any entity or system capable of expressing a gene, including but not limited to an organism, a cell, a seed, or a cell-free or in vitro expression system.

The term "recombinant" refers to an artificial combination of two otherwise separated segments of sequence, e.g., by chemical synthesis or by the manipulation of isolated segments of nucleic acids by genetic engineering techniques.

The term "polypeptide fragment" refers to a sub-portion of a polypeptide or protein. All terms defined herein relating to "polypeptide," unless otherwise specified, apply equally to "polypeptide fragment."

The phrase "derived from," used in reference to a polypeptide, means that the polypeptide was generated by a gene that was cloned or otherwise obtained from a specified organism or synthesized de novo or recombined in a manner in which the polypeptide is identical to or substantially similar to that obtained from the organism.

The phrase "derived from," used in reference to a sample, means that the sample can be physically traced to a specified source, whether or not it is in an altered form. For example, a sample which is a lysate of a specific cell is "derived from" the cell.

The term "immunogenic" refers to the ability of a substance (antigen) to induce an immune response.

The phrase "specifically binds," used in reference to antibodies that specifically bind 45-desaturase proteins or polypeptide fragments thereof, means that the antibody does not bind other front end desaturase enzymes, such as Δ4-desaturase, Δ6-desaturase, or Δ8-desaturase, or polypeptide fragments thereof. The phrase "specifically binds" does not exclude binding of antibodies to Δ5-desaturase from more than one organism such as fungi or algae.

All references to singular characteristics or limitations of the embodiments described herein shall include the corresponding plural characteristic or limitation, and vice versa, unless otherwise specified or clearly implied to the contrary by the context in which the reference is made.

All combinations of method or process steps as described herein may be performed in any order, unless otherwise specified or clearly implied to the contrary by the context in which the referenced combination is made.

The embodiments described herein may comprise, consist of, or consist essentially of the essential elements of the invention described herein, as well as any additional or optional ingredients, components, or limitations described herein or otherwise useful for Δ5-desaturase-specific antibodies.

All U.S. patents and publications referred to herein are hereby incorporated in their entirety by reference.

Antibodies

The embodiments described herein comprise antibodies that specifically bind Δ5-desaturase. The nature of the specificity is such that the antibodies do not bind other "front end" desaturases, such as Δ6-desaturase.

The Δ5-desaturase-specific antibodies described herein comprise antibodies that bind Δ5-desaturase from more than one type of organism. For example, the antibodies bind Δ5-desaturase derived from fungus or algae. More specifically, among fungi, the antibodies bind Δ5-desaturase derived from *Saprolegnia diclina* and/or *Mortierella alpina*. More specifically, the antibodies bind Δ5-desaturase having the polypeptide sequence of SEQ ID NO: 1.

The Δ5-desaturase-specific antibodies described herein also bind full-length Δ5-desaturases that are homologous to, or variants of, Δ5-desaturase derived from *Saprolegnia diclina* having the polypeptide sequence of SEQ ID NO: 1. For example, the antibodies bind Δ5-desaturases having about 50% identity, about 60% identity, about 70% identity, about 80% identity, or about 90% identity to the polypeptide sequence of SEQ ID NO: 1. The amino acid residues that may be substituted are determined by the definition of "conservative variation" or "homologous" described herein.

In addition to binding the full-length Δ5-desaturase protein, the antibodies described herein also bind Δ5-desaturase polypeptide fragments. Such fragments may include about 5%, 10%, 20%, 30%, 40%, 50%, 60%, 70%, 80%, or 90% of the full-length protein.

The antibodies described herein bind Δ5-desaturase polypeptide fragments derived from fungus or algae. More specifically, among fungi, the antibodies bind Δ5-desaturase polypeptide fragments derived from *Saprolegnia diclina* and/or *Mortierella alpina*. More specifically, the antibodies bind Δ5-desaturase polypeptide fragments having the polypeptide sequence of SEQ ID NO: 2.

The Δ5-desaturase-specific antibodies described herein also bind Δ5-desaturase polypeptide fragments that are homologous to, or variants of, the Δ5-desaturase polypeptide fragment having the polypeptide sequence of SEQ ID NO: 2. For example, the antibodies may bind Δ5-desaturase polypeptide fragments having about 50% identity, about 60% identity, about 70% identity, about 80% identity, or about 90% identity to the polypeptide sequence of SEQ ID NO: 2.

The amino acid residues that may be substituted are determined by the definition of "conservative variation" or "homologous" described herein.

The 5-desaturase-specific antibodies described herein also bind Δ5-desaturase polypeptide fragments comprising at least about 4 contiguous amino acid residues of a polypeptide fragment having the sequence of SEQ ID NO: 2 or conservative variations of SEQ ID NO: 2. The antibodies may also bind fragments comprising at least about 8, 15, 30, 60, or 90 contiguous amino acid residues of a polypeptide fragment having the sequence of SEQ ID NO: 2 or conservative variations of SEQ ID NO: 2.

The antibodies described herein may be polyclonal or monoclonal.

Methods of Producing Antibodies that Specifically Bind Δ5-Desaturase

The embodiments described herein also comprise methods of producing antibodies that specifically bind Δ5-desaturase.

The methods comprise a first step of immunizing an animal with a polypeptide fragment and a second step of isolating the antibody from the animal. The step of immunizing is well-known in the art of generating antibodies. The step of isolating the antibody is well-known in the art of protein purification. Any animal that produces an immune response to the polypeptide fragments disclosed herein may be used.

In one embodiment, the immunizing step comprises immunizing an animal with a polypeptide fragment derived from fungus or algae. More specifically the immunizing step comprises immunizing an animal with a polypeptide fragment derived from *Saprolegnia diclina* and/or *Mortierella alpina*. More specifically, the immunizing step comprises immunizing an animal with a polypeptide fragment having the polypeptide sequence of SEQ ID NO: 2.

In another embodiment, the immunizing step comprises immunizing an animal with a polypeptide fragment comprising at least 8 contiguous amino acid residues of SEQ ID NO: 2 or conservative variations of SEQ ID NO: 2.

The immunizing step may also comprise immunizing an animal with polypeptide fragments that are homologous to, or variants of, the polypeptides having the polypeptide sequence of SEQ ID NO: 2. For example, animals may be immunized with polypeptides having 50% identity, about 60% identity, about 70% identity, about 80% identity, or about 90% identity to the polypeptide sequence of SEQ ID NO: 2. The amino acid residues that may be substituted are determined by the definition of "conservative variation" or "homologous" described herein.

The immunizing step may also comprise immunizing an animal with polypeptide fragments comprising at least about 4 contiguous amino acid residues of a polypeptide fragment having the sequence of SEQ ID NO: 2 or conservative variations of SEQ ID NO: 2. The animals may also be immunized with fragments comprising at least about 8, 15, 30, 60, or 90 contiguous amino acid residues of a polypeptide fragment having the sequence of SEQ ID NO: 2 or conservative variations of SEQ ID NO: 2.

Polyclonal antibodies may be generated by the method described in the examples. Monoclonal antibodies may be generated by the method described in U.S. Pat. No. 5,256,561, which is incorporated herein by reference in its entirety. Briefly, isolated GST-His-SDD5-C1 polypeptides as produced in Example 3 are used as an immunogen to immunize mice. The immunization regimen (10 mice) comprises primary immunization with additional immunizations on days 14 and 29. For each immunization, 10 μg of 0.1% sodium dodecyl sulfate (SDS)-solubilized peptide is emulsified with Ribi adjuvant. The emulsified immunogen is inoculated intraperitoneally and subcutaneously. Individual mice are screened for microtiter plate enzyme immunoassay (EIA) immunoreactivity by standard well-known methods with the immunogen approximately four weeks after the third immunization. Fifteen weeks after the third immunization, mice are inoculated intravenously with 10 μg of immunogen.

Three days after the intravenous boost, splenocytes are fused with Sp2/0-Ag14 myeloma cells obtained from MRC Laboratory of Molecular Biology (Cambridge, England) using the polyethylene glycol (PEG) method. The fusions are cultured in Iscove's Modified Dulbecco's Medium (IMDM) containing 10% fetal calf serum (FCS), plus 1% hypoxanthine, aminopterin and thymidine (HAT). Bulk cultures are screened by microtiter plate EIA using the immunogen solubilized in 6M guanidine HCl. Reactive cultures are subcloned and screened. GST-His polypeptides purified from the expression vector pET41a(+) (Novagen, Madison, Wis.) are used in the screening microtiter plate format to identify and eliminate monoclonal antibody-secreting clones reactive with the GST-His component of the of GST-His-SDD5-C1 fusion protein. Thus, the clones selected for final expansion are reactive with the SDD5-C1 component of recombinant of GST-His-SDD5-C1 proteins. Such clones are expanded, aliquoted and frozen in IMDM containing 10% FCS and 10% dimethylsulfoxide.

The following procedures are used in the production and purification of monoclonal antibodies. Frozen hybridoma cells are thawed and placed into expansion culture. Viable hybridoma cells are inoculated intraperitoneally into pristane-treated mice. Ascites fluid is removed from the mice, pooled, filtered through a 0.2-μm filter and subjected to an immunoglobulin class G (IgG) analysis to determine the volume of the Protein A column required for the purification. Filtered and thawed ascites fluid is mixed with an equal volume of Protein A sepharose binding buffer (1.5 M glycine, 3.0 M NaCl, pH 8.9) and re-filtered through a 0.2-μm filter. The volume of the Protein A column is determined by the quantity of IgG present in the ascites. The ascites is then applied to the Protein A chromatography column (available from GE Healthcare, Piscataway, N.J.), and the column is washed with the above binding buffer. Washing is continued until a stable absorbance (280 nm) baseline is obtained. The antibody is eluted from the Protein A column with 0.1 M citric acid, pH 4.5. The eluate is dialyzed against PBS overnight at 2-8° C. The dialyzed IgG is sterile-filtered, dispensed in aliquots, and stored at −80° C.

Methods of Detecting Δ5-Desaturase in a Sample

The embodiments described herein also encompass methods of detecting Δ5-desaturase in a sample. A first step includes exposing the sample to an antibody wherein the exposing is performed under conditions that allow binding of the antibody to Δ5-desaturase. A second step includes detecting a bound antibody.

Another version of the detection method further comprises a third step. The third step includes quantitating the bound antibody detected in the second step. This can be performed using any of the detection methods described below, wherein the level of signal derived from the detecting step can be compared to a standard curve performed on standards with known amounts of enzyme to obtain an quantitation of Δ5-desaturase in the sample.

The first step may comprise exposing the sample to any of the antibodies described herein under conditions that allow binding of the antibody to any of the polypeptides or polypeptide fragments described herein. The conditions that allow binding of the antibody to polypeptides or polypeptide fragments are well known in the art.

The samples may comprise any sample in which the presence of Δ5-desaturase is suspected. Such samples include but are not limited to plants, plant seeds, yeast, microorganisms, algae, fungi, and mammalian cells, whether expressing Δ5-desaturase natively, through a transgene, or through a foreign vector. For example, the sample may comprise a seed extract, an extract from a transgenic seed, a host suspected of expressing a heterologous Δ5-desaturase, or any sample derived from an organism or host that natively expresses Δ5-desaturase. The preparation of samples for detection of proteins in the sample is well known the art.

The antibodies described herein can be used in any assay or detection method known in the art using antibodies. Such methods include but are not limited to immunoprecipitation, particle immunoassays, immunonephelometry, enzyme immunoassays (EIAs), radioimmunoassays (RIAs), fluorescent immunoassays (FIAs), chemiluminescent immunoassays, western blotting, and enzyme-linked immunoassays (ELISAs). These assays can be used for detection only or detection and quantitation of an amount of a protein in a sample. The use of these and other immunoassays for detecting proteins in samples is well known the art (see Sambrook et al., "Molecular Cloning: A Laboratory Manual, Second Edition (1989), Cold Spring Harbor Laboratory Press, Cold Spring Harbor, N.Y.)).

In addition to the methods described in the Examples, other antibody-based formats for detecting a protein, such as Δ5-desaturase, in a sample are described in U.S. Pat. No. 6,818,392, which is incorporated herein by reference. These methods are summarized as follows.

In one assay, an anti-Δ5-desaturase "capture antibody" or a fragment thereof is coated onto a solid phase (e.g., a microparticle, a microtiter well, a bead, etc.). A test sample is then contacted with the antibody such that, if Δ5-desaturase is present in the patient sample, antibody/Δ5-desaturase complexes are formed as a first mixture. A conjugate comprising a "probe antibody" attached to a signal-generating compound is then added. The probe antibody binds an epitope on Δ5-desaturase distinct from and compatible with the epitope bound by the capture antibody. Antibody/Δ5-desaturase/antibody probe complexes are then formed as a second mixture. Δ5-desaturase is then detected in the sample by detecting the presence of the signal generated by the antibody/Δ5-desaturase/antibody probe complexes. The amount of Δ5-desaturase(s) in the test sample may also be calculated, as the signal generated is proportional to the amount of Δ5-desaturase in the sample. Another manner of detecting the complexes formed is to utilize a conjugate comprising a third antibody attached to a signal-generating compound. In particular, once the antibody/Δ5-desaturase/antibody complexes described above have formed (i.e., the latter antibody being the "second antibody" and unlabelled), one may then add a conjugate which binds to the second, unlabeled antibody in solution. The conjugate may comprise, for example, an antigen or anti-antibody attached to a signal-generating compound capable of generating a detectable signal that is capable of binding to the bound second antibody. Detection of the signal indicates presence of the complexes and thus presence of Δ5-desaturase in the sample. The signal generated is proportional to the amount of Δ5-desaturase present in the sample. (See, e.g., U.S. Pat. No. 6,015,662.)

The initial capture antibody used in the immunoassays may be covalently or non-covalently (e.g., ionic, hydrophobic, etc.) attached to the solid phase. Linking agents for covalent attachment are known in the art and may be part of the solid phase or derivatized to it prior to coating. Examples of solid phases used in immunoassays are porous and non-porous materials, latex particles, magnetic particles, microparticles, beads, membranes, microtiter wells and plastic tubes. The choice of solid phase material and method of labeling the antigen or antibody present in the conjugate, if desired, is determined based upon desired assay format performance characteristics.

As noted above, the conjugate (or indicator reagent) may comprise an antibody (or perhaps anti-antibody, depending upon the assay), attached to a signal-generating compound or label. This signal-generating compound or "label" is in itself detectable or may be reacted with one or more additional compounds to generate a detectable product. Examples of signal-generating compounds include chromogens, radioisotopes (e.g., $^{125}$I, $^{131}$I, $^{32}$P, $^{3}$H, $^{35}$S, and $^{14}$C), chemiluminescent compounds (e.g., acridinium), particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use (e.g., alkaline phosphatase or horseradish peroxidase), addition of a chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Additionally, the antibodies of the present invention may be used in detection systems using fixed cells or fixed tissues, with appropriate labeling of each anti-Δ5-desaturase antibody. In particular, the tissue sample is contacted with a conjugate comprising a signal-generating compound attached to one of the anti-Δ5-desaturase antibodies described herein in order to form a mixture. The mixture is then incubated for a time and under conditions sufficient for Δ5-desaturase/antibody complexes to form. The presence of Δ5-desaturase present in the sample is determined by detecting the signal generated. This particular format may be altered by adding an unlabeled anti-Δ5-desaturase antibody to the cell or tissue followed by a labeled secondary antibody against the anti-Δ5-desaturase antibody.

The antibodies described herein may also be used for purifying Δ5-desaturase, for example, by affinity chromatography. Anti-Δ5-desaturase antibodies may be attached to or immobilized on a substrate or support. The solution containing Δ5-desaturase is then contacted with the immobilized antibody for a time and under conditions suitable for the formation of immune complexes between the antibody and polypeptides containing Δ5-desaturase. Unbound material is separated from the bound immune complexes. The complexes of Δ5-desaturase are then separated from the support.

Peptides and Nucleotides

The present invention encompasses immunogenic isolated polypeptides consisting essentially of SEQ ID NO: 2 or conservative variations of SEQ ID NO: 2. Other peptide sequences may be added upstream or downstream of SEQ ID NO: 2 or conservative variations of SEQ ID NO: 2. In addition to glutathione S-transferase (GST) and 6×-histidine (6×-His) tag (SEQ ID NO: 17) sequences, as described below, any peptide sequence or chemical modification can be added that does not inhibit the ability of the peptide to be expressed and purified in sufficient quantities or otherwise be suitable for production of antibodies that specifically recognize Δ5-desaturase.

The present invention also encompasses isolated nucleic acids having sequences that encode an immunogenic polypeptide consisting essentially of SEQ ID NO: 2 or conservative variations of SEQ ID NO: 2. One exemplary sequence is SEQ ID NO: 3. Due to the degeneracy of the genetic code, other sequences that encode immunogenic polypeptides consisting essentially of SEQ ID NO: 2 or conservative variations of SEQ ID NO: 2 are readily apparent. In addition to nucleotide sequences encoding GST and 6×-His (SEQ ID NO: 17) peptide sequences, any nucleotide sequence can be added that does that does not inhibit the ability of the encoded peptide to be expressed and purified in sufficient quantities or otherwise be suitable for production of antibodies that specifically recognize Δ5-desaturase.

EXAMPLE 1

Selection of Polypeptide Sequences from *Saprolegnia diclina* Δ5-Desaturase for Antibody Production As described above, the full-length Δ5-desaturase enzyme (SDD5) is not suitable for antibody production due to its high degree of hydrophobicity. The present inventors therefore sought to identify a fragment of Δ5-desaturase suitable for generating antibodies that recognize the full-length Δ5-desaturase protein. The Δ5-desaturase amino acid sequence from *Saprolegnia diclina* (SEQ ID NO: 1) was analyzed using the "proteinlounge" program (www.proteinlounge.com) to identify hydrophilic regions on the protein that may be surface exposed and hence immunogenic. The analysis revealed two relatively hydrophilic regions. Peptides corresponding to the regions (SDD5 Construct 1: SDD5-C1 and SDD5 Construct 2: SDD5-C2) were selected, purified in large quantities, and used for antibody production as described in Examples 3 and 4. The full-length amino acid sequence of SDD5 from *S. diclina* and the amino acid and nucleotide sequences of the SDD5-C1 and SDD5-C2 polypeptides are as follows:

*Saprolegnia diclina* Δ5-desaturase (SDD5) (SEQ ID NO: 1):

(SEQ ID NO: 1)
MAPQTELRQRHAAVAETPVAGKKAFTWQEVAQHNTAASAWIIIRGKVYDV

TEWANKHPGGREMVLLHAGREATDTFDSYHPFSDKAESILNKYEIGTFTG

PSEFPTFKPDTGFYKECRKRVGEYFKKNNLHPQDGFPGLWRMMVVFAVAG

LALYGMHFSTIFALQLAAAALFGVCQALPLLHVMHDSSHASYTNMPFFHY

VVGRFAMDWFAGGSMVSWLNQHVVGHHIYTNVAGSDPDLPVNMDGDIRRI

VNRQVFQPMYAFQHIYLPPLYGVLGLKFRIQDFTDTFGSHTNGPIRVNPH

ALSTWMAMISSKSFWAFYRVYLPLAVLQMPIKTYLAIFFLAEFVTGWYLA

FNFQVSHVSTECGYPCGDEAKMALQDEWAVSQVKTSVDYAHGSWMTTFLA

GALNYQVVHHLFPSVSQYHYPAIAPIIVDVCKEYNIKYAILPDFTAAFVA

HLKHLRNMGQQGIAATIHMG

SDD5-Construct 1 (SDD5-C1) (SEQ ID NO: 2) $M_1 \rightarrow F_{136}$ of SEQ ID NO: 1; 136 aa):

(SEQ ID NO: 2)
MAPQTELRQRHAAVAETPVAGKKAFTWQEVAQHNTAASAWIIIRGKVYDV

TEWANKHPGGREMVLLHAGREATDTFDSYHPFSDKAESILNKYEIGTFTG

PSEFPTFKPDTGFYKECRKRVGEYFKKNNLHPQDGF

SDD5-C1 nucleotide sequence (408 bp) (SEQ ID NO: 3):

(SEQ ID NO: 3)
5' ATGGCCCCGCAGACGGAGCTCCGCCAGCGCCACGCCGCCGTCGCCGA

GACGCCGGTGGCCGGCAAGAAGGCCTTTACATGGCAGGAGGTCGCGCAGC

ACAACACGGCGGCCTCGGCCTGGATCATTATCCGCGGCAAGGTCTACGAC

GTGACCGAGTGGGCCAACAAGCACCCCGGCGGCCGCGAGATGGTGCTGCT

GCACGCCGGTCGCGAGGCCACCGACACGTTCGACTCGTACCACCCGTTCA

GCGACAAGGCCGAGTCGATCTTGAACAAGTATGAGATTGGCACGTTCACG

GGCCCGTCCGAGTTTCCGACCTTCAAGCCGGACACGGGCTTCTACAAGGA

GTGCCGCAAGCGCGTTGGCGAGTACTTCAAGAAGAACAACCTCCATCCGC

AGGACGGCTTC 3'

SDD5-Construct 2 (SDD5-C2) SEQ ID NO: 4) ($N_{220} \rightarrow H_{300}$ of SEQ ID NO: 1; 81 aa):

(SEQ ID NO: 4)
NQHVVGHHIYTNVAGSDPDLPVNMDGDIRRIVNRQVFQPMYAFQHIYLPP

LYGVLGLKFRIQDFTDTFGSHTNGPIRVNPH

SDD5-C2 nucleotide sequence (243 bp) (SEQ ID NO: 5):

(SEQ ID NO: 5)
5' AACCAGCACGTCGTGGGCCACCACATCTACACGAACGTCGCGGGCTC

GGACCCGGATCTTCCGGTCAACATGGACGGCGACATCCGCCGCATCGTGA

ACCGCCAGGTGTTCCAGCCCATGTACGCATTCCAGCACATCTACCTTCCG

CCGCTCTATGGCGTGCTTGGCCTCAAGTTCCGCATCCAGGACTTCACCGA

CACGTTCGGCTCGCACACGAACGGCCCGATCCGCGTCAACCCGCAC 3'

The SDD5-C1 polypeptide and nucleotide sequences identified in this example comprise an exemplary immunogenic polypeptide and an exemplary nucleotide encoding an immunogenic polypeptide for generating antibodies that specifically recognize Δ5-desaturase.

EXAMPLE 2

Cloning of Polypeptide Sequences from *Saproleonia diclina* Δ5-Desaturase into Expression Vectors for *E. coli* and Baculovirus Generation of SDD5-C1 and SDD5-C2 Constructs for Expression in *E. coli*.

Gene fragments encoding the SDD5-C1 and SDD5-C2 regions of Δ5-desaturase were cloned in-frame into the *E. coli* expression vector pET41a(+) (Novagen, Madison, Wis.). The pET41a(+) vector contains a T7 promoter followed by an N-terminal glutathione S-transferase (GST) tag, a 6×-histidine (6×-His) tag (SEQ ID NO: 17), and an enterokinase cleavage site upstream of NcoI (5') and EcoRI (3') sites.

The 411-bp SDD5-C1 and 249-bp SDD5-C2 fragments were amplified from pRSP3, which contains the full-length sdd5 gene (the pYX242 vector [Novagen] containing the sdd5 gene), with the primers shown in Table 1.

TABLE 1

Primers Used in Amplifying SDD5-C1 and SDD5-C2 Gene Fragments from pRSP3

| Primer | Sequence | SEQ ID NO: |
|---|---|---|
| SDD5-C1-NcoI-FP | 5'-AGA GTC CCA TGG CCC CGC AGA C-3' | 6 |
| SDD5-C1-EcoRI-RP | 5'-TGT ACA GAA TTC TTA GAA GCC GTC C-3' | 7 |
| SDD5-C2-NcoI-FP | 5'-AGA GTC CCA TGG GGA ACC AGC ACG-3' | 8 |
| SDD5-C2-EcoRI-RP | 5'-TGT ACA GAA TTC TTA GTG CGG GTT GAC-3' | 9 |

Cloning sites are underlined.

The primers were designed to amplify the 411-bp SDD5-C1 and the 249-bp SDD5-C2 domains from the full-length gene. The forward primers (ending with "FP" in Table 1) contained start codons (ATG) in-frame with the gene and NcoI sites upstream of the start codons (underlined in Table 1). The reverse primers (ending with "RP" in Table 1) contained stop codons (TAA) and EcoRI sites (underlined in Table 1). The NcoI and EcoRI sites were incorporated in the primers to clone the genes into the pET41a vector downstream of the GST and 6x-His tags.

The SDD5-C1 and SDD5-C2 domains were amplified using Pwo DNA Polymerase (Roche Applied Science, Indianapolis, Ind.) and 10xPCRx Enhancer Solution (Invitrogen, Carlsbad, Calif.). Water purified with the "MILLI-Q"-brand water system (Millipore Corporation, Billerica, Mass.) was used for all PCR reactions described herein. The PCR reaction conditions were as follows:

PCR reaction mix:

| pRSP3 plasmid | 0.5 µl (~100 ng) |
|---|---|
| Forward primer (80 µM) | 1 µl |
| Reverse primer (80 µM) | 1 µl |
| 2.5 mM dNTPs | 4 µl |
| 10X PCR buffer | 5 µl |
| 10X PCRx Enhancer | 5 µl |
| Pwo DNA Polymerase | 0.5 µl (2.5 U) |
| Water | 33 µl |

PCR cycling conditions:
94° C. (7 min)
94° C. (45 s), 58° C. (45 s), 72° C. (1 min)—for 30 cycles
72° C. (15 min)

The PCR amplicons (411-bp SDD5-C1 and 249-bp SDD5-C2) were cloned into the NcoI and EcoRI sites of the pET41a (+) vector using methods well-known in the art. Recombinant clones were identified by colony PCR. Plasmid DNA was isolated from 2 recombinant clones (Strain: *E. coli* DH5 alpha) and sequenced completely.

Generation of GST-SDD5-C1 and GST-SDD5-C2 Constructs for Expression in Insect Cells pFastBacl(+) (Invitrogen, Carlsbad, Calif.) is a vector used for expression in insect cells using a polyhedrin promoter. Since this is a native vector, it does not contain a GST tag and the thrombin cleavage site (L-V-P-R-G-S)↓ (SEQ ID NO: 18). We introduced a GST tag-thrombin cleavage site cassette into the EcoRI (5')/HindIII (3') sites of the vector, which was then used for expression of the SDD5-C1 and SDD5-C2 GST-fusion proteins (GST-SDD5-C1 and GST-SDD5-C2, respectively). Upon cleavage with thrombin, two amino acid residues (Gly and Ser) were left behind at the N-terminal end of the protein.

For the generation of GST-SDD5-C1, GST was fused to the N-terminus of the SDD5-C1 by overlap PCR. The fusion fragment was then cloned into the Eco RI/Hind III sites of the pFastBac vector. To generate the GST-SDD5-C1 fragment, two fragments, a GST-thrombin cleavage site fragment (GST fragment) and an SDD5-C1 fragment, were generated.

The GST fragment was amplified from pGEX-4T (GE Healthcare, Piscataway, N.J.) using the primers listed in Table 2.

TABLE 2

Primers Used in Amplifying the GST Fragment from pGEX-4T

| Primer | Sequence | SEQ ID NO: |
|---|---|---|
| GST-EcoRI-FP | 5' AGC GCG CGG AAT TCA TGT CCC CTA TAC 3' | 10 |
| GST-RP | 5' GGA TCC ACG CGG AAC CAG ATC CGA TTT TGG AGG ATG GT 3' | 11 |

The EcoRI site is underlined in the GST-EcoRI-FP primer, and the thrombin cleavage site is underlined in the GST-RP primer.

The GST fragment was amplified using "PLATINUM" Pfx-brand polymerase (Invitrogen, Carlsbad, Calif.) and 10xPCRx Enhancer Solution (Invitrogen). The PCR reaction conditions were as follows:

PCR reaction mix:

| pGEX-4T1 plasmid | 0.5 µl (~100 ng) |
|---|---|
| GST-EcoRI-FP (80 µM) | 1 µl |
| GST-RP (80 µM) | 1 µl |
| 2.5 mM dNTPs | 4 µl |
| 10X PCR buffer | 5 µl |
| 10X PCRx Enhancer | 10 µl |
| MgSO$_4$ (50 mM) | 1 µl |
| "PLATINUM" Pfx-brand polymerase | 0.5 µl (1.25 U) |
| Water | 27 µl |

PCR cycling conditions
94° C. (5 min)
94° C. (45 s), 56° C. (45 s), 72° C. (45 s)—for 29 cycles
72° C. (15 min)

The PCR-amplified GST fragment (~700 bp) was gel purified.

The SDD5-C1 fragment was amplified from the full-length SDD5 plasmid, pRSP3, using the primers listed in Table 3.

TABLE 3

Primers Used in Amplifying the SDD5-C1 Fragment from pRSP3

| Primer | Sequence | SEQ ID NO: |
|---|---|---|
| pFast-sdd5-C1-FP | 5' *AAA TCG GAT CTG GTT CCG* CGT GGA TCC ATG GCC CCG C3' | 12 |
| pFast-sdd5-C1-RP | 5' ATA GTA AAG CTT TCA GAA GCC GTC CTG CGG AT 3' | 13 |

In pFast-sdd5-C1-FP, the thrombin site is underlined, and letters in italics indicate GST sequence. In pFast-sdd5-C1-RP, the HindIII site is underlined.

The SDD5-C1 fragment was amplified using "PLATI-NUM" Pfx-brand polymerase (Invitrogen, Carlsbad, Calif.) and 10×PCRx Enhancer Solution (Invitrogen, Carlsbad, Calif.). The PCR reaction conditions were as follows:

PCR reaction mix:

| | |
|---|---|
| pRSP3 plasmid | 0.5 µl (~100 ng) |
| pFast-sdd5-C1-FP (80 µM) | 1 µl |
| pFast-sdd5-C1-RP (80 µM) | 1 µl |
| 2.5 mM dNTPs | 4 µl |
| 10X PCR buffer | 5 µl |
| 10X PCR Enhancer | 10 µl |
| MgSO₄ (50 mM) | 1 µl |
| "PLATINUM" Pfx-brand polymerase | 0.5 µl (1.25 U) |
| Water | 27 µl |

PCR cycling conditions:

94° C. (5 min)

94° C. (45 s), 56° C. (45 s), 72° C. (45 s)—for 29 cycles

72° C. (15 min)

The PCR-amplified SDD5-C1 fragment (~420 bp) was gel purified.

The GST-SDD5-C1 fusion was generated by overlap PCR. For overlap PCR, equimolar ratios of the gel purified PCR fragments (GST and SDD5-C1) from the initial reactions were used as template, and "PLATINUM" Pfx-brand polymerase (Invitrogen, Carlsbad, Calif.) was used for amplification with the GST-EcoRI-FP and pFast-sdd5-C1-RP primers (see Tables 2 and 3, respectively).

PCR reaction mix:

| | |
|---|---|
| Gel-purified GST fragment (700 bp) | 2 µl (~30 ng) |
| Gel-purified SDD5-C1 fragment (400 bp) | 2 µl (~15 ng) |
| GST-EcoR-I-FP (80 µM) | 1 µl |
| pFast-sdd5-C1-RP (80 µM) | 1 µl |
| 2.5 mM dNTPs | 4 µl |
| 10X PCR buffer | 5 µl |
| "PLATINUM" Pfx-brand polymerase | 1 µl (2.5 U) |
| Water | 34 µl |

PCR cycling conditions:

94° C. (2 min)

94° C. (1 min), 58° C. (1 min), 72° C. (1 min)—for 30 cycles

72° C. (15 min)

Overlap PCR yielded an amplicon of ~1.1 kb as expected. The 1.1-kb amplicon was gel-purified and digested with EcoRI and HindIII enzymes. The digested PCR fragment was then cloned into the EcoRI/HindIII sites of the pFastBac vector using methods known in the art. Recombinant clones were identified by colony PCR, and plasmid DNA was isolated from two recombinant clones (Strain: *E. coli* DH5 alpha).

For the generation of GST-SDD5-C2, GST was fused to the N-terminus of the SDD5-C2 (GST-SDD5-C2) by overlap PCR. The fusion fragment was then cloned into the EcoRI/Hind III sites of the pFastBac vector. To generate the GST-SDD5 fragment, two fragments, the GST fragment described above and an SDD5-C2 fragment, were generated.

The GST fragment was amplified from pGEX-4T1 using the GST-EcoRI-FP (SEQ ID NO: 10) and GST-RP (SEQ ID NO: 11) primers as described above.

The SDD5-C2 fragment was amplified from the full-length SDD5 plasmid, pRSP3, using the primers listed in Table 4.

TABLE 4

Primers Used in Amplifying the SDD5-C2 Fragment from pRSP3

| Primer | Sequence | SEQ ID NO: |
|---|---|---|
| pFast-sdd5-C2-FP | 5' AAA *TCG GAT CTG GTT CCG* <u>CGT GGA</u> TCC AAC CAG CAC G 3' | 14 |
| pFast-sdd5-C2-RP | 5' TGT ATC <u>AAG CTT</u> TCA GTG CGG GTT GAC G 3' | 15 |

In pFast-sdd5-C2-FP, the thrombin site is underlined, and letters in italics indicate GST sequence. In pFast-sdd5-C2-RP, the HindIII site is underlined.

The SDD5-C2 fragment was amplified using "PLATI-NUM" Pfx-brand polymerase (Invitrogen, Carlsbad, Calif.) and 10×PCRx Enhancer Solution (Invitrogen, Carlsbad, Calif.). The PCR reaction conditions were as follows:

PCR reaction mix:

| | |
|---|---|
| Full-length SDD5 plasmid | 0.5 µl (~100 ng) |
| pFast-sdd5-C2-FP (80 µM) | 1 µl |
| pFast-sdd5 C2-RP (80 µM) | 1 µl |
| 2.5 mM dNTPs | 4 µl |
| 10X PCR buffer | 5 µl |
| 10X PCR Enhancer | 10 µl |
| MgSO₄ (50 mM) | 1 µl |
| "PLATINUM" Pfx-brand polymerase | 0.5 µl (1.25 U) |
| Water | 27 µl |

PCR cycling conditions

94° C. (5 min)

94° C. (45 s), 56° C. (45 s), 72° C. (45 s)—for 29 cycles

72° C. (15 min)

The PCR-amplified SDD5-C2 fragment (~249 bp) was gel purified.

The GST-SDD5-C2 fusion was generated by overlap PCR. For overlap PCR, equimolar ratios of the gel-purified PCR fragments (GST and SDD5-C2) from the initial reactions were used as template and "PLATINUM" Pfx-brand polymerase (Invitrogen, Carlsbad, Calif.) was used for amplification with the GST-EcoRI-FP and pFast-sdd5-C2-RP primers (see Tables 2 and 4, respectively).

PCR reaction mix:

| | |
|---|---|
| Gel-purified GST fragment (700 bp) | 2 µl (~45 ng) |
| Gel-purified SDD5-C2 fragment (249 bp) | 2 µl (~15 ng) |
| GST-EcoRI-FP (80 µM) | 1 µl |
| pFast-sdd5-C2-RP (80 µM) | 1 µl |
| 2.5 mM dNTPs | 4 µl |
| 10X PCR Buffer | 5 µl |
| "PLATINUM" Pfx-brand polymerase | 1 µl (2.5 U) |
| Water | 34 µl |

PCR cycling conditions

94° C. (2 min)

94° C. (1 min), 58° C. (1 min), 72° C. (1 min)—for 30 cycles

72° C. (15 min)

Overlap PCR yielded an amplicon of ~950 bp as expected. The 950-bp amplicon was gel-purified and digested with EcoRI and HindIII enzymes and cloned into the EcoRI/Hind III sites of the pFastBac vector. Recombinant clones were identified by colony PCR and plasmid DNA was isolated from two recombinant clones (Strain: *E. coli* DH5 alpha).

This example provides suitable materials and methods for generating expression vectors for use in expressing the SDD5-C1 and SDD5-C2 polypeptides in *E. coli* or insect cells.

EXAMPLE 3

Expression and Purification of SDD5-C1 and SDD5-C2 Polypeptides

Optimization of Expression and Purification Conditions of SDD5 Constructs in *E. coli*

BL21 Star (DE3) "ONE-SHOT"-brand *E. coli* cells (Invitrogen) were selected for expression studies. These cells have the following genotype: F-ompT hsdS$_B$(r$_B$-m$_B$-) gal dcm me131 (DE3). Derived from *E. coli* strain B, these cells are the most widely used host for producing proteins and have the advantage of being naturally deficient in both Lon and ompT proteases. This strain advantageously lacks me131, one of the major sources of mRNA degradation, which improves the stability of mRNA and enhances protein expression.

To determine optimal conditions for expression, the two SDD5 recombinant constructs (pET41a(+)-SDD5-C1 and pET41a(+)-SDD5-C2) were transformed in BL21 Star (DE3) "ONE-SHOT"-brand *E. coli* cells. As a control, pET41a(+) alone was used for transformation. Optimization of expression conditions of SDD5 constructs was carried out for each construct on a small scale (5 ml) using different experimental conditions (temperatures of 20° C., 30° C., or 37° C.; isopropyl β-D-1-thiogalactopyranoside (IPTG) concentrations of 0.1 mM, 0.25 mM, or 0.5 mM; and times of induction of either 3 hrs or 6 hrs). All the expression studies were carried out in LB broth. Induced cells were lysed using "BUGBUSTER"-brand lysis solution (Novagen), and the soluble and insoluble fractions loaded onto 12% SDS-PAGE and stained with Coomassie blue. The expected sizes of the fusion proteins were 46 kDa for the C1 construct (GST-His-SDD5-C1) and 39 kDa for the C2 construct (GST-His-SDD5-C2).

Expression was observed in all conditions in the insoluble fraction. The highest expression for both constructs occurred with incubation at 37° C. with 0.1 mM IPTG for 3 hrs.

To verify the ability to purify the expressed fusion proteins, small-scale purification of GST-His-SDD5-C1 and GST-His-SDD5-C2 was performed under optimal expression conditions in *E. coli*. Induction was carried out for each construct in 50 ml of LB containing 50 ug/ml kanamycin (in 250-ml flasks) at an OD$_{600}$ of 0.6 using 0.1 mM IPTG for 3 hrs at 37° C. The induced cell pellets were lysed by sonication, and the insoluble fraction was pelleted. The pellets (inclusion bodies) were washed with 0.1% Triton X-100 and denatured using 50 ml of 8 M urea. The solubilized C1 and C2 fusion proteins were purified using Ni-NTA affinity chromatography, and the bound proteins were eluted in 8 M urea buffer containing 250 mM imidazole. The eluted fractions were analyzed on 12% SDS-PAGE, as shown in FIG. 1. The fractions were pooled, and yields were estimated using Bradford's method. The concentration of GST-His-SDD5-C1 was 12 mg/L, and the concentration of GST-His-SDD5-C2 was 40 mg/L.

Expression of GST-SDD5-C1 and GST-SDD5-C2 Peptides in Insect Cell Lines

The sequence-confirmed GST-SDD5-C1 and GST-SDD5-C2 constructs in the pFastBac vector (Invitrogen) were used for the generation of recombinant bacmid by transposition in "MAX EFFICIENCY"-brand DH10Bac *E. coli* competent cells (Invitrogen). Recombinant bacmids, selected on X-Gal/IPTG plates with kanamycin, gentamycin, and tetracycline, were analyzed for gene integration by PCR using M13 and appropriate gene specific primers. These bacmids were then used for transfection into Sf9 cells.

Sf9 cells were transfected with the GST-SDD5-C1 and GST-SDD5-C2 constructs in the pFastBac vector. Five microliters of bacmid DNA were mixed with 5 μl of "CELL-FECTIN"-brand transfection reagent (Invitrogen) for transfection in Sf9 cells in 6 wells plate (0.8×10$^6$ cells/well). The cells were incubated for 4 days to generate P1 virus. Amplification of P1 virus (2×10$^6$ cells/ml) was carried out in 100-ml suspension culture to obtain P2 stage virus in 4 days.

Expression screening of each of the four constructs was carried out in 24-Well Deep Well Plates (Promega, Madison, Wis.) in two cell lines, Sf9 and "HIGH FIVE"-brand cells (Invitrogen). Each well in the 24-Well Deep Well plate, was seeded with 4 ml of insect cells (3×10$^6$ cells/ml). The cells were infected with the recombinant virus of GST-SDD5-C1 and GST-SDD5-C2 constructs at three different multiplicities of infection (MOI) (0.5, 2, and 5) and two time points (48 and 72 hrs). The infected cells were collected by centrifugation at each time point for purification of the recombinant protein.

Small scale purification of recombinant proteins in the cell pellets were carried out by affinity chromatography using Glutathione Sepharose 4B (GE Healthcare) as follows: Cells were resuspended in 1 ml of cold lysis buffer (1×PBS, pH 7.4 containing 1 mM PMSF, 10 μ/ml leupeptin and 10 μg/ml pepstatin) and ruptured by sonication. The lysed cells were centrifuged (13,000 rpm for 10 minutes at 4° C.) and the supernatant fraction was collected. The supernatant was incubated with 50 μl of GST-Sepharose beads (pre-equilibrated with 1×PBS) at 4° C. for 1 hour. The samples were spun and the collected beads were washed three times with 1 ml each of cold 1×PBS. The washed GST-Sepharose beads were resuspended in 40 μl of 20 mM glutathione solution (in 50 mM Tris-HCl, pH 8) to elute bound proteins. The eluted proteins were analyzed on 12% SDS-PAGE. The expected size of GST-SDD5-C1 fusion protein was ~37.9 kDa, and the expected size of the GST-SDD5-C2 fusion protein was ~31.9 kDa.

Expression of the GST-fusion proteins was best at an MOI of 2.0 for 48 hours for all the four constructs in "HIGH FIVE"-brand cells (except for SDD5-C2), and the expression level was negligible for all the constructs in Sf-9 insect cells.

Table 5 shows the comparison of the four constructs in *E. coli* versus in insect cells. The expression level of fusion protein was low in insect cells. Therefore, large scale purification of the fusion proteins was carried out in *E. coli*.

TABLE 5

Comparison of Expression of Constructs in *E. coli* vs. Insect Cells

| Construct | Expression system | Extrapolated yield of GST fusion protein |
|---|---|---|
| SDD5-C1 | *E. coli* | 12 mg/l |
|  | "HIGH FIVE"-brand cells | 1.2 mg/l |
| SDD5-C2 | *E. coli* | 40 mg/l |
|  | "HIGH FIVE"-brand cells | negligible |

Large-Scale Expression and Purification of GST-His-SDD5-C1 and GST-His-SDD5-C2 in *E. coli*

Expression of GST-His-SDD5-C1 and GST-His-SDD5-C2 was performed with BL21 Star (DE3) "ONE-SHOT"-brand *E. coli* cells in 1 L of LB broth with 50 ug/ml kanamycin. The cells were induced at an OD$_{600}$ with 0.1 mM IPTG for 3 hrs at 37° C. in a shaker (250 rpm).

The induced culture was centrifuged at 5000 rpm for 15 min, and the pellet was washed with Tris buffer (10 mM Tris

[pH 7.5], 100 mM NaH$_2$PO$_4$). The pellet was resuspended in 60 ml of Tris buffer and lysis was carried out using four freeze-thaw cycles of the pellet in liquid N$_2$, followed by sonication. The lysed culture was centrifuged at 12000 rpm for 30 min to obtain the inclusion bodies.

The inclusion bodies were washed thrice with 0.1% Triton X-100 and twice with Tris buffer prior to solubilization. Solubilization of inclusion bodies was carried out using 60 ml of solubilizing buffer (10 mM Tris-Cl [pH 7.5], 100 mM NaH$_2$PO$_4$, 6 M GuHCl, 15 mM imidazole] with shaking at room temperature for 1 hr.

Affinity chromatography was performed using 5 ml Ni-IDA columns ("HISTRAP"-brand FF Columns, GE Healthcare, Piscataway, N.J.). The column was equilibrated with 10 column volumes of the solubilizing buffer. Following solubilization of the inclusion bodies, the sample was centrifuged at 12000 rpm for 30 min and the supernatant was loaded onto the column at the flow rate of 1 ml/min. The column was washed sequentially with five column-volumes of lysis buffer and Buffer 1 (10 mM Tris-Cl [pH 7.5], 100 mM NaH$_2$PO$_4$, 6 M GuHCl, 30 mM imidazole) at a flow rate of 3 ml/min. Gradient elution was performed (3 ml/min) with increasing concentration of imidazole using Buffer 1 and Buffer 2 (10 mM Tris-Cl [pH 7.5], 100 mM NaH$_2$PO$_4$, 6 M GuHCl, 350 mM imidazole) in a total elution volume of 50 ml. The protein eluate was collected as 5 ml fractions and analyzed by SDS-PAGE.

In order to remove guanidine hydrochloride and imidazole, the fusion proteins were subjected to dialysis using Tris buffer. Ten milliliters of the sample (~10 mg) were dialyzed using 3.5 kD molecular weight cutoff membrane against 1 L of Tris buffer for 2 hrs at 4° C. The buffer was changed and the samples were dialyzed overnight against 3 L of the same buffer. With both constructs, the majority of the protein precipitated during dialysis. The precipitates were washed with sterile water and lyophilized. The lyophilized proteins were to be resuspended in appropriate volumes of buffer containing 6 M GdHCl for immunization.

Figure 2:
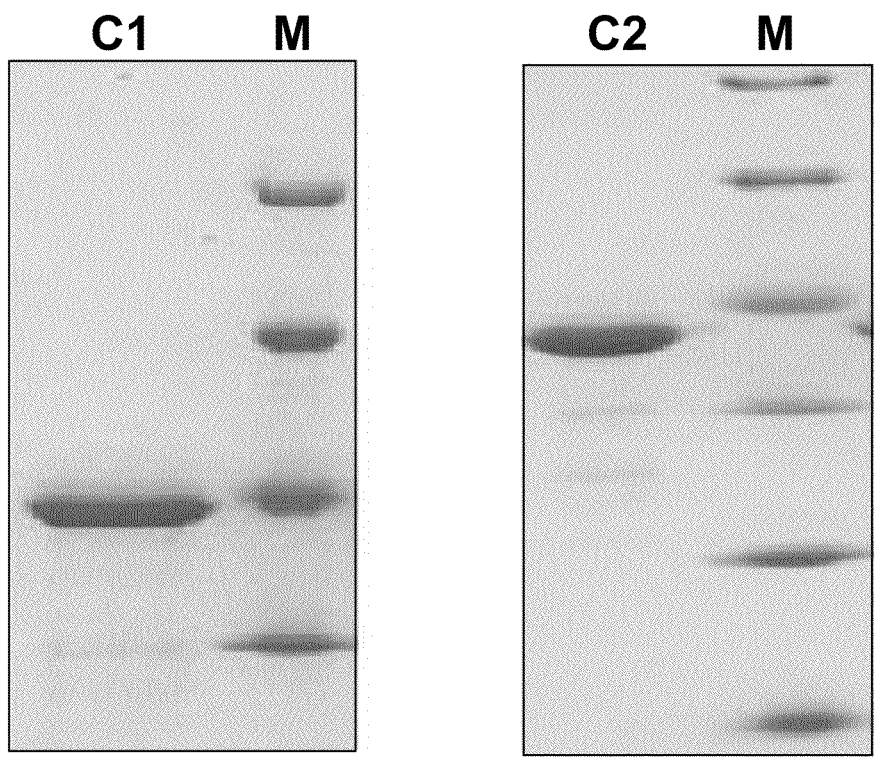
FIG. 2 shows an SDS-PAGE gel of *E. coli*-expressed GST-His-SDD5-C1 and GST-His-SDD5-C2 polypeptides stained with Coomassie blue after purification of inclusion bodies under denatured conditions using nickel affinity chromatography.

A small aliquot of each of the lyophilized sample was used for estimation of protein yield by Bradford's method using bovine serum albumin (BSA) as a standard. The purity was determined visually on SDS-PAGE stained with Coomassie, as shown in FIG. 2. Ten milligrams of purified SDD5-C1 and seven milligrams of purified SDD5-C2 were obtained by expression in *E. coli* (see Table 6) and were used for generation of antibodies.

TABLE 6

Proteins as Lyophilized Samples

| SEQ ID NO: | Protein | Molecular weight | Quantity | Purity |
|---|---|---|---|---|
| 1 | GST-His-SDD5-C1 | 47.2 KDa | 10.0 mg | >90% |
| 2 | GST-His-SDD5-C2 | 41.1 KDa | 7.0 mg | >95% |

This example provides materials and methods for expressing and purifying the SDD5-C1 and SDD5-C2 polypeptides in quantities suitable for antibody production.

EXAMPLE 4

Generation of Antibodies Against GST-His-SDD5-C1 and GST-His-SDD5-C2 in Rabbits

Antibody Production

Polyclonal antibody production was performed using two New Zealand white rabbits per peptide using a 77-day protocol at Covance Research Center (Denver, Pa.). A pre-bleed sample was collected from each rabbit before the start of the study to obtain a baseline titer. Samples were stored at −70° C. The peptides were dissolved in buffer containing 6 M guanidine at a concentration of 1 mg/ml, aliquoted, and stored at −70° C. Doses of 500 µg of the appropriate peptide were injected in the respective rabbits at the subcutaneous nodal area, pitts, and groin regions. Further booster doses of 500 µg peptides were given on Day 21 at the subcutaneous and intramuscular regions, Day 42 at the subcutaneous neck region, and Day 63 at the subcutaneous dorsal region. Production bleeds (approximately 20 ml/rabbit) were collected two times, on Day 51 and on day 72. Enzyme-linked immunosorbant assays (ELISAs) were performed to determine the antibody titer (see below). Terminal bleeds (approximately 55 ml/rabbit) were collected by exsanguination on day 82. The terminal bleeds from both rabbits injected with the same peptide were pooled and a fraction was used for further purification procedures. The remaining production and terminal bleeds were stored at −70° C.

ELISA Test for Antibody Titer

ELISAs for determining antibody titers in the bleeds were performed as follows. Antigen was diluted in phosphate-buffered saline (PBS) to obtain a final concentration of 1 ug/mL and applied to the ELISA plate. A solution of PBS+3% BSA was used for non-specific blocking and diluting sample, control, and secondary antibodies. The sample serum was run against a negative control comprised of either the specific pre-immune sera (usually used in the first assay only) or normal sera (used in subsequent assays). The dilution of the initial serum sample started at 1:500 with a 5-fold serial dilution down the plate. All subsequent serum sample dilutions (i.e., bleed #2) were determined by the titer of the previous sera sample. If the serum sample was a pre-screen, a 1:10, 5-fold dilution was used. Negative controls were also 1:10, 5-fold dilutions. A positive control was run (anti-ovalbumin developed in rabbit) in at least 3 wells at a dilution of 1:1000. The mean value in optical density (O.D.) of the wells was reported as the positive control (the typical O.D. range was between 1.9 and 2.4). The titers were detected using HRP-conjugated secondary antibodies and ABTS peroxidase substrate system (KPL, Gaithersburg, Md.). The plate was read at a wavelength of 415 nm with a reference at 570 nm. The titers for each rabbit are presented in Tables 7 and 8 as the 50% Titer, which is the dilution of the antibody that gave 50% of the maximum achieved response. The 50% Titer values were based on a Logit regression fit to the full data set.

TABLE 7

EIA Titer Assay Results for SDD5-C1 Antigen

| | |
|---|---|
| Species: | NZW Rabbit |
| Immunogen: | SDD5-C1 |
| Plate Coating Ag: | SDD5-C1 |
| Concentration: | 1 ug/mL |

TABLE 7-continued

EIA Titer Assay Results for SDD5-C1 Antigen

| Samples | | Control (negative) | Control (positive) |
|---|---|---|---|
| Bleed Type: | Production | Bleed Type: Pre | anti-ovalbumin (rabbit) |
| Bleed Date: | Jul. 24, 2008 | Bleed Date: May 28, 2008 | diluted at 1:1000 |
| Animal ID | 50% Titer Samples | Control (negative) | MeanValue (O.D.) Control (positive) |
| BA 046 | 62,000 | <100 | 2.2 |
| BA 047 | 102,000 | <100 | |
| Blank: | 0.049 | | |
| Blank Std Dev: | 0.009 | | |
| Noise Cutoff: | 0.076 | | |

TABLE 8

EIA Titer Assay Results for SDD5-C2 Antigen

| Species: | NZW Rabbit |
| Immunogen: | SDD5-C2 |
| Plate Coating Ag: | SDD5-C2 |
| Concentration: | 1 ug/mL |

| Samples | | Control (negative) | Control (positive) |
|---|---|---|---|
| Bleed Type: | Production | Bleed Type: Pre | anti-ovalbumin (rabbit) |
| Bleed Date: | Jul. 24, 2008 | Bleed Date: May 28, 2008 | diluted at 1:1000 |
| Animal ID | 50% Titer Samples | Control (negative) | MeanValue (O.D.) Control (positive) |
| BA 048 | 62,000 | <100 | 2.33 |
| BA 049 | 32,000 | <100 | |
| Blank: | 0.050 | | |
| Blank Std Dev: | 0.006 | | |
| Noise Cutoff: | 0.069 | | |

This example shows that the SDD1-C1 and SDD2-C2 polypeptides can be used to generate serum with a high antibody titer.

EXAMPLE 5

Depletion of GST-Specific Antibodies from the Polyclonal Antibodies

The terminal bleeds were pooled for the two rabbits in each group to proceed with purification of Δ5-desaturase antibodies. An antigen-specific purification was run first to reduce the amount of material that must be run over the GST column. This affinity purified product was then passed through a GST column to remove the anti-GST antibodies.

Column apparatuses were prepared by pouring GST resin into column housing. Two 5-mL immobilized GST columns were used per 20 mL of sera (terminal bleed). The columns were equilibrated with binding/wash buffer (1×PBS). Using a 1:1 dilution, PBS was added to the antiserum. The PBS/antiserum solution was run over the column very slowly, and the flow-through material was collected into a beaker labeled as "unbound." After all the serum was run over the column, the column was washed using an appropriate amount of PBS. The wash was monitored by measuring the absorbance at 280 nm. When the absorbance was less than or equal to 0.05 above background, the anti-GST antibodies were eluted using 6M guanidine-HCl. The eluate was collected in 7-10 mL fractions. The absorbance of the fractions was measured at 280 nm to verify which fractions contained the undesired anti-GST antibodies. These steps were repeated twice until the recovery assay read around 1% or less.

A recovery assay was performed by coating the ELISA plate with GST in sterile PBS-plate coating buffer for 16-24 hours at 4° C. After washing the plates with PBS containing 0.05% Tween-20 wash buffer, the plates were blocked with PBS containing 3% bovine serum albumin fraction V for 1 hour at room temperature. The plates were washed again with the wash buffer before adding normalized dilutions of unbound antibodies (antibody fractions obtained after passing over GST columns) and incubated at 37° C. for 1 hour. The titers were detected using HRP-conjugated secondary antibodies and ABTS peroxidase substrate system (KPL, Gaithersburg, Md.). The plate was read at a wavelength of 415 nm with a reference at 570 nm to confirm the complete removal of anti-GST antibodies from the purified products. The results are shown in Tables 9 and 10.

TABLE 9

Anti-GST Depletion ELISA Data for SDD5-C1

| Product Description: | Rabbit Immunoglobulin (Ig) affinity purified and buffer exchanged from 40 ml of sera. |
|---|---|

| TECHNICAL DATA | |
|---|---|
| Protein Concentration: | 0.34 mg/ml ($A_{280\ nM}$, $\epsilon$ = 1.4 ml/mg cm) |
| Product Volume: | ~7.8 ml |
| Buffer: | Phosphate buffered saline, pH 7.4 (no |

TABLE 9-continued

Anti-GST Depletion ELISA Data for SDD5-C1

| | preservative) | |
|---|---|---|
| Purity: | Unknown | |
| Sterility: | Not sterile | |

Quality Control (of GST unbound):

| Results | 50% Titer | % Recovery |
|---|---|---|
| Starting Material | 20436.71 | n/a |
| Bound | 81.91 | 0% |
| Wash | 28.91 | 0.1% |

TABLE 10

Anti-GST Depletion ELISA Data for SDD5-C2

| Product Description: | Rabbit Immunoglobulin (Ig) affinity purified and buffer exchanged from 40 ml of sera. |
|---|---|

TECHNICAL DATA

| Protein Concentration: | 0.47 mg/ml ($A_{280\ nM}$, $\epsilon$ = 1.4 ml/mg cm) |
|---|---|
| Product Volume: | ~1.5 ml |
| Buffer: | Phosphate buffered saline, pH 7.4 (no preservative) |
| Purity: | Unknown |
| Sterility: | Not sterile |

Quality Control (of GST unbound):

| Results | 50% Titer | % Recovery |
|---|---|---|
| Starting Material | 1701.59 | n/a |
| Bound | 1.1 | 0% |
| Wash | 22.48 | 1.3% |

This example provides methods for removing antibodies specifically recognizing the GST epitope from the antibodies generated against the GST-His-SDD5-C1 and GST-His-SDD5-C2 polypeptides.

EXAMPLE 6

Characterization of Polyclonal Antibodies for Cross Reactivity Towards Full-Length S. diclina Δ5-Desaturase Once the polyclonal antibodies were depleted of anti-GST antibodies (described in Example 5), the remaining polyclonal antibodies were tested for cross reactivity towards the recombinant, full-length S. diclina Δ5-desaturase (SDD5) expressed in transgenic yeast. Because SDD5 is a membrane-bound desaturase, it localizes in the microsomal fraction of cells, like other membrane-bound proteins. Thus, it was necessary to isolate microsomes from yeast expressing the sdd5 gene in order to obtain the SDD5 protein for analysis.

Saccharomyces cerevisiae YPH499 cells were transformed with either pYX242 vector (control) (Novagen, Madison, Wis.) or pYX242 containing the S. diclina Δ5-desaturase gene (pRSP3) by lithium acetate-mediated transformation using the "FROZEN-EZ YEAST TRANSFORMATION II"-brand transformation kit (Zymo Research, Orange, Calif.). Transformed cells were selected for their ability to grow on medium lacking leucine. Single colonies from the transformed cells were grown for 2 days at 28° C. in 3 ml of medium consisting of 0.08% (w/v) complete supplement mixture without leucine (CSM-LEU, BIO 101, Vista, Calif.), 0.17% (w/v) yeast nitrogen base without amino acids (BD Diagnostic Systems, Sparks, Md.), 0.5% (w/v) ammonium sulfate, and 2% (w/v) dextrose. These cultures were then used to inoculate 250 ml of the same growth medium to an $OD_{600}$≈0.2. After 24 hours of growth with shaking (~250 rpm at 28° C.), cells were collected by centrifugation and resuspended in 10 ml of 50 mM HEPES (pH 7.5), 50 mM NaCl, 20% (w/v) sucrose, 1 mM EDTA (pH 8.0), 2 mM DTT, 1 mM PMSF, and 100 μl of protease inhibitor cocktail (Sigma-Aldrich, cat. no. P9599). To the resuspended cells, 5 ml of 0.5 mm glass beads were added. Cells were then disrupted by 10 cycles of 30-sec vortexing at top speed and chilling on ice for 30 sec. The lysed cells were then centrifuged at 10,000×g for 15 minutes. An aliquot of the resulting supernatant was removed for western blot analysis, and the remainder of the supernatant was subjected to ultracentrifugation at 100,000×g for two hours. The microsomal pellet from this spin was resuspended in 500 μl of buffer consisting of 50 mM HEPES (pH 7.5) and 50 mM NaCl. The protein concentration of the 10,000×g supernatant and the resuspended microsomal pellet were determined spectrophotometrically at $OD_{595}$ using the Bio-Rad Protein Assay reagent (Hercules, Calif.).

Western blotting was performed as follows. Aliquots of the 10,000×g supernatant, the microsomal pellet, purified GST-His-SDD5-C1 peptide, and GST-His-SDD5-C2 peptide were electrophoresed on 12% SDS-PAGE. Proteins were transferred from the gel to "IMMOBILON"-P-brand PVDF membrane (Millipore, Billerica, Mass.) by electroblotting. The blot was blocked for one hour at room temperature with 1× Blotto (Santa Cruz Biotechnology, Santa Cruz, Calif.) (5% w/v dried milk dissolved in TBST) and then probed with dilutions (1:500) of the immunopurified SDD5-C1 or SDD5-C2 antisera. Following three five-minute washes in TBST, the blot was probed for one hour with diluted goat anti-rabbit IgG (1:10,000) linked to alkaline phosphatase (secondary antibody; Sigma-Aldrich, St. Louis, Mo.). The blot was then washed with TBST as above, and developed by addition of the "BCIP"/NBT-brand Blue Liquid alkaline phosphatase substrate (Sigma-Aldrich).

Figure 3:
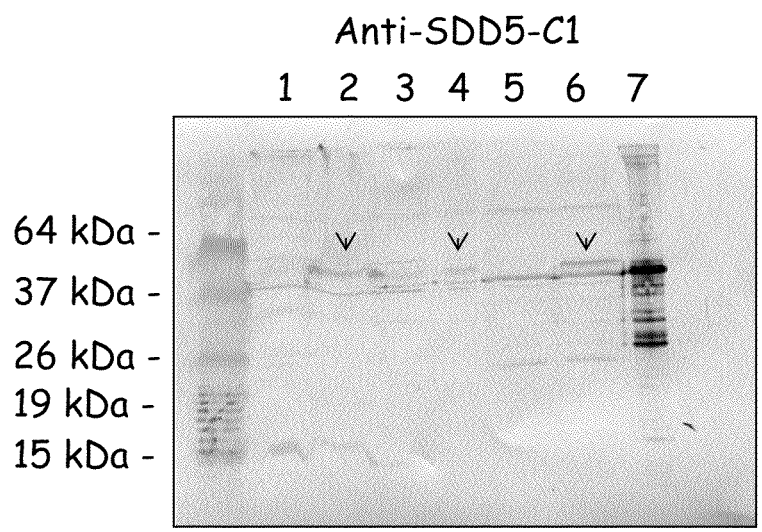
FIG. 3 shows a western blot of extracts from yeast transfected with pRSP3 (pYX242+sdd5) or vector alone (pYX242) probed with anti-SDD5-C1 antibodies.

FIG. 3 shows a western blot of proteins obtained from yeast microsomes extracted from transgenic yeast expressing either pRSP3 (pYX242+S. diclina Δ5 desaturase gene, sdd5) or vector alone (pYX242) using anti-SDD5-C1 antibodies as a probe. A ~50 kDa band, corresponding to the molecular weight of SDD5, was detected with the anti-SDD5-C1 antibodies in microsomal extracts from yeast expressing pRSP3 (FIG. 3, lanes 2 and 4) but not in extracts from yeast expressing the pYX242 control (FIG. 3, Lanes 1 and 3). This ~50 kDa band was also detected in supernatants obtained from yeast expressing pRSP3 after the low-speed spin (10,000×g) (FIG. 3, Lane 6), but not in the supernatants of the pYX242-containing control yeast (FIG. 3, Lane 5). Because supernatants obtained after low-speed spins contain microsomes, which is the region in the cell where membrane bound desaturases (e.g. SDD5) localize, this result indicates that the antibodies recognize the full-length S. diclina Δ5-desaturase enzyme in its native form. This antibody also reacts with the GST-His-SDD5-C1 peptide, which was used to generate the antibody (FIG. 3, Lane 7).

Figure 4:
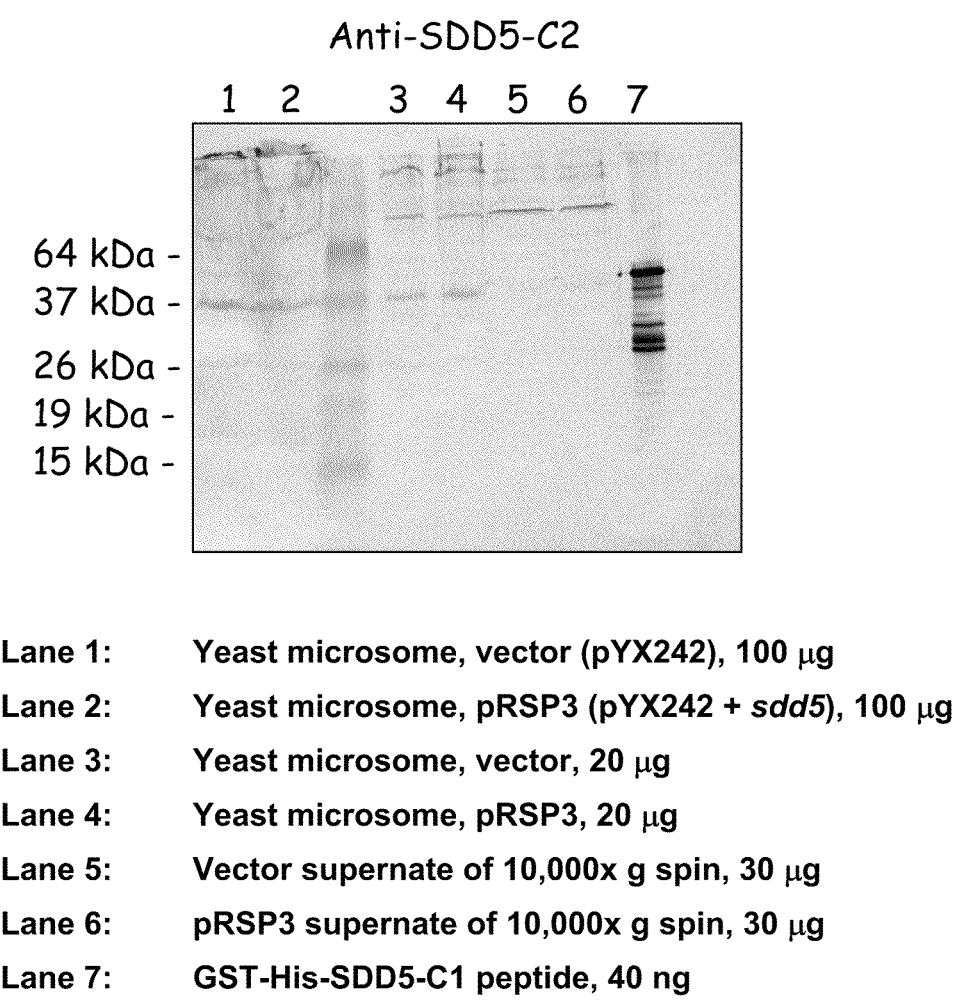
FIG. 4 shows a western blot of extracts from yeast transfected with pRSP3 (pYX242+sdd5) or vector alone (pYX242) using anti-SDD5-C2 antibodies.

FIG. 4 shows a western blot of proteins obtained from yeast microsomes extracted from transgenic yeast expressing either pRSP3 (pYX242+sdd5) or vector alone (pYX242) using anti-SDD5-C2 antibodies as a probe. Here, the ~50 KDa band corresponding to SDD5 could not be detected in extracts from yeast expressing pRSP3 (FIG. 4, Lanes 2, 4, and 6), as compared to controls. This indicates that the antibodies generated against the SDD5-C2 peptide could not recognize the SDD5 protein.

Figure 5:
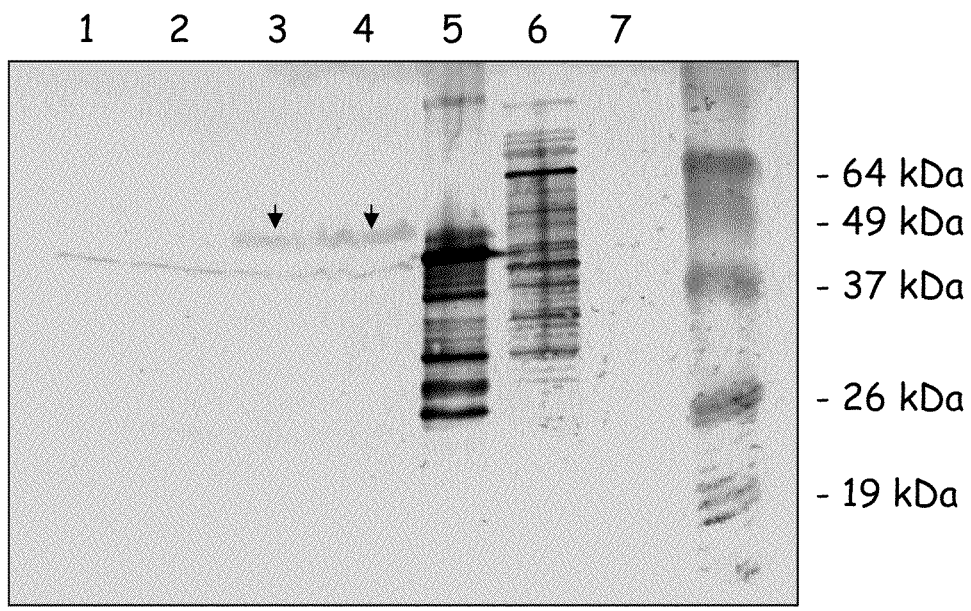
FIG. 5 shows a western blot of extracts from yeast transfected with pRSP3 (pYX242+sdd5) pRSP1 (pYX242+sdd6), or vector alone (pYX242) using anti-SDD5-C1 antibodies.

To determine if the anti-SDD5-C1 antibody cross-reacts with *Saprolegnia diclina* Δ6-desaturase (SDD6), pRSP1, expression of SDD6 was performed in yeast with an expression vector containing the SDD6 gene, pRSP1 (pYX242+sdd6). Microsomes were extracted from the transgenic yeast and evaluated by immunoblotting using the anti-SDD5-C1 antibody as a probe. FIG. 5 shows that this antibody does not recognize the *S. diclina* Δ6-desaturase, as no specific ~50-kDa bands were visualized in the microsomal extracts (FIG. 5, Lane 7). In contrast, a ~50 k-Da band corresponding to SDD5 was recognized by the anti-SDD5-C1 antibody in yeast microsomal fractions expressing the SDD5 gene (pRSP3) only (FIG. 5, Lanes 3 and 4). No ~50-kDa protein bands were detected in pYX242 control lanes that do not contain the SDD5 protein (FIG. 5, Lanes 1 and 2).

FIG. 6 shows an alignment of the SDD5-C1 polypeptide (amino acid residues 1-136 of *Saprolegnia diclina* Δ5-desaturase) with the corresponding N-terminal region of *Mortierella alpina* Δ5-desaturase (SEQ ID NO: 16; amino acid residues 1-118 of GenBank Accession No. 074212). Because these regions are highly homologous and display >35% sequence identity, the antibodies against SDD5-C1 will likely cross react with the *M. alpina* Δ5-desaturase protein and other related Δ5-desaturase proteins with conserved epitopes, such as those derived from algae or other organisms.

As shown herein, an antibody that cross-reacts with the full-length *S. diclina* Δ5-desaturase and fragments thereof has been successfully generated. The antibody does not cross-react with the *S. diclina* Δ6-desaturase. This Δ5-desaturase-specific antibody can thus be used to selectively detect and quantitate Δ5-desaturase proteins that are expressed transgenically in heterologous hosts such as plants, plant seeds, yeast, mammalian cells, etc, that produce ARA, EPA, or DHA. This antibody can also be used to recognize the native Δ5-desaturase protein present in organisms that naturally produce PUFAs, including microorganisms, algae, fungi, and mammalian cells.

It is understood that the invention is not confined to the particular protocols, constructs, and arrangements of elements herein illustrated and described, but embraces all modified forms thereof as come within the scope of the following claims.

What is claimed is:

1. An isolated antibody generated against SEQ ID NO: 2, wherein the isolated antibody specifically binds a Δ5-desaturase comprising the polypeptide sequence of SEQ ID NO: 2 and specifically binds at least 8 contiguous amino acid residues of SEQ ID NO: 2, and wherein said Δ5-desaturase is derived from fungus or algae.

2. The isolated antibody of claim 1 wherein the antibody specifically binds Δ5-desaturase derived from *Saprolegnia diclina* or *Mortierella alpina*.

3. The isolated antibody of claim 1 wherein the antibody specifically binds full-length Δ5-desaturase derived from fungus or algae.

4. The isolated antibody of claim 1 wherein the antibody is polyclonal.

5. The isolated antibody of claim 1 wherein the antibody is monoclonal.

6. The isolated antibody of claim 1 wherein the Δ5-desaturase polypeptide fragment is derived from fungus or algae.

7. The isolated antibody of claim 6 wherein the Δ5-desaturase polypeptide fragment is derived from *Saprolegnia diclina* or *Mortierella alpina*.

8. The isolated antibody of claim 6 wherein the antibody is polyclonal.

9. The isolated antibody of claim 6 wherein the antibody is monoclonal.

10. An isolated antibody generated against a polypeptide fragment selected from SEQ ID NO: 2 and SEQ ID NO: 4, wherein the isolated antibody specifically binds a Δ5-desaturase, said Δ5-desaturase comprising the polypeptide sequence of SEQ ID NO: 2, wherein the antibody does not bind Δ6-desaturase, and wherein both said Δ5-desaturase and said Δ6-desaturase are derived from fungus or algae.

11. The antibody of claim 10 wherein the antibody specifically binds Δ5-desaturase derived from *Saprolegnia diclina* or *Mortierella alpina*.

12. The antibody of claim 10 wherein the antibody specifically binds full-length Δ5-desaturase derived from fungus or algae.

13. The antibody of claim 10 wherein the antibody is polyclonal.

14. The antibody of claim 10 wherein the antibody is monoclonal.

15. An isolated antibody generated against a polypeptide fragment selected from SEQ ID NO: 2 and SEQ ID NO: 4, wherein said isolated antibody specifically binds a Δ5-desaturase comprising the polypeptide sequence of SEQ ID NO: 2.

16. The isolated antibody of claim 15, wherein the Δ5-desaturase is derived from *Saprolegnia diclina* or *Mortierella alpina*.

17. The isolated antibody of claim 15, wherein the Δ5-desaturase is derived from fungus or algae.

18. The isolated antibody of claim 15, wherein the isolated antibody does not bind Δ6-desaturase.

19. An isolated antibody generated against a polypeptide fragment, said isolated antibody isolated from an animal after immunizing said animal with said polypeptide fragment, wherein said isolated antibody specifically binds a Δ5-desaturase comprising the polypeptide sequence of SEQ ID NO: 2, and wherein said polypeptide fragment is selected from SEQ ID NO: 2 and SEQ ID NO: 4.

* * * * *